(12) United States Patent
Edel et al.

(10) Patent No.: US 8,295,025 B2
(45) Date of Patent: Oct. 23, 2012

(54) APPARATUS AND METHOD FOR CONTROLLING EXCITATION FREQUENCY OF MAGNETOSTRICTIVE ULTRASONIC DEVICE

(76) Inventors: Alan Edel, Petach Tikva (IL); Julian Edel, Petach Tikva (IL); Simeon Chavkin, Petach Tikva (IL)

( * ) Notice: Subject to any disclaimer, the term of this patent is extended or adjusted under 35 U.S.C. 154(b) by 492 days.

(21) Appl. No.: 12/461,630

(22) Filed: Aug. 19, 2009

(65) Prior Publication Data

US 2010/0277848 A1 Nov. 4, 2010

Related U.S. Application Data

(63) Continuation-in-part of application No. 11/351,436, filed on Feb. 13, 2006, now Pat. No. 7,715,167.

(60) Provisional application No. 60/655,103, filed on Feb. 23, 2005.

(51) Int. Cl.
*H01H 47/00* (2006.01)
*A61C 1/07* (2006.01)
(52) U.S. Cl. ........................................ 361/157; 433/119
(58) Field of Classification Search .................. 361/157; 433/119
See application file for complete search history.

(56) References Cited

U.S. PATENT DOCUMENTS

| 5,754,016 | A | * | 5/1998 | Jovanovic et al. | ............ 318/118 |
| 6,819,027 | B2 | * | 11/2004 | Saraf | ........................ 310/316.01 |
| 2002/0107538 | A1 | * | 8/2002 | Shibata et al. | ................ 606/169 |
| 2003/0222535 | A1 | * | 12/2003 | Gofman et al. | .......... 310/316.01 |

* cited by examiner

*Primary Examiner* — Jared Fureman
*Assistant Examiner* — Scott Bauer

(57) ABSTRACT

Apparatus and method for controlling the frequency of the current in the excitation coil of a handpiece of a dental magnetostrictive ultrasonic scaling unit, or a similar transducer. A microprocessor continually samples predetermined functions of the current through the excitation coil, and periodically adjusts the frequency, by performing a coarse-stepped frequency scan, followed by a fine-stepped frequency scan until the function samples are close to predetermined optimum values. The functions can include the peak of the current and the peak of a high-pass filtered version of the current. The frequency adjustment is performed each time the handpiece is energized by the practitioner, and at frequent intervals thereafter, assuring automatic optimal frequency at all times and under all conditions. Apparatus according to the invention does not require sensing coils or complex power- or impedance-sensing circuitry and covers a wide range of resonant frequencies for different handpiece- and insert types. A configuration with multiple handpieces is supported.

3 Claims, 7 Drawing Sheets

APPARATUS AND METHOD FOR CONTROLLING EXCITATION FREQUENCY OF MAGNETOSTRICTIVE ULTRASONIC DEVICE

The present application is continuation-in-part of U.S. patent application Ser. No. 11/351,436, filed on Feb. 13, 2006 now U.S. Pat. No. 7,715,167 and published on Aug. 24, 2006 as Pub. No. US2006/0188841; it claims benefit of U.S. Provisional Patent Application No. 60/655,103 filed Feb. 23, 2005.

FIELD OF THE INVENTION

The present invention relates to controllers for ultrasonic transducers and, more particularly, to the control of the excitation frequency of a magnetostrictive ultrasonic transducer for dental use.

BACKGROUND OF THE INVENTION

The use of a magnetostrictive transducer for an ultrasonic dental device, such as a dental scaler, is well-known and standardized throughout the dental profession. Such devices are characterized by having a handpiece into which a removable insert with a working tip is placed. The handpiece contains an excitation coil which is electrically connected via a cable to a control unit, or controller, that provides the excitation energy to the coil. The removable insert contains a stack of plates of magnetostrictive material which expands and contracts when subjected to a time-varying magnetic field. A suitable time-varying magnetic field is created by directing a time-varying electrical current through the excitation coil surrounding the inserted tip, and thereby vibrations are induced in the insert and carried to the tip. The vibrating tip is then used by the practitioner in dental work, a non-limiting example of which is to remove calculus from the surface of teeth.

Although the fundamental concept as described above is widely employed in the same basic form, there is considerable variation in the manner by which the excitation current is controlled, in particular the frequency of the time-varying excitation current. The removable insert has a resonant frequency related to the natural acoustic modes of vibration of the magnetostrictive stack contained therein, and it is desirable to excite vibrations within the insert at or near the resonant frequency. Doing so will optimize the vibrational energy in the insert, and will thus optimize the magnitude of the tip vibration for most efficient use in cleaning the teeth.

There are in practice two common sizes of insert, having resonant frequencies of approximately 25 KHz and 30 KHz, respectively. It is thus desirable that the controller be able to generate time-varying currents at or near each of these frequencies. A number of different device configurations have been developed to accommodate this requirement.

U.S. Pat. No. 5,151,085 to Sakurai, et al. (herein denoted as "Sakurai") discloses an oscillator for driving an ultrasonic transducer, wherein the oscillator is controlled by feedback from a multi-winding transformer. The transducer of Sakurai, however, is not of the magnetostrictive variety, and does not feature an excitation coil. Instead, Sakurai relies on a rather complex arrangement of inductors, transformers, and amplifiers to detect and match the impedance of the transformer. The handpiece disclosed in Sakurai has no excitation coil; moreover, the controller disclosed in Sakurai is not compatible with magnetostrictive inserts.

Likewise, U.S. Pat. No. 5,180,363 to Idemoto, et al. (herein denoted as "Idemoto") discloses a complex system built around an oscillator featuring impedance-matching transformers and a phase-locked loop for detecting phase mismatch in the feedback signal. As with Sakurai, Idemoto's handpiece lacks an excitation coil; the transducer disclosed in Idemoto is not of the magnetostrictive variety; moreover, Idemoto's controller is incompatible with magnetostrictive inserts.

U.S. Pat. No. 5,451,161 to Sharp (herein denoted as "Sharp '161") discloses a magnetostrictive insert with an excitation coil and a transformer for providing feedback to a transistor oscillator. In the oscillator of Sharp '161, the transistor collector-emitter current flows through the primary winding of the transformer, and also through the excitation coil, which is in series with the transformer's primary. The current induced in the secondary winding of the transformer flows into the base of the transistor, thereby causing the oscillator to oscillate near the resonant frequency of the magnetostrictive insert. The oscillator frequency, however, is not precisely at the resonance point of the insert, because there are additional components involved in the feedback circuit which have energy storage effects. Thus, the oscillator frequency is the resonant frequency of the entire circuit, not that of just the magnetostrictive insert itself. Furthermore, the oscillator of Sharp '161 has a limited range of operation, and normally can accommodate only inserts having a restricted range of resonant frequencies. Therefore, to allow the controller to be utilized with inserts having a resonant frequency of 25 KHz as well as inserts having a resonant frequency of 30 KHz, Sharp '161 provides a switchable capacitance in the transformer's secondary circuit, to provide the oscillator with two frequency ranges. Thus, Sharp '161 requires the practitioner to change the switch setting when changing from one type of insert to the other.

U.S. Pat. No. 5,730,594, also to Sharp (herein denoted as "Sharp '594"), partially overcomes the limitations of Sharp '161 by providing a phase-locked loop oscillator to provide automatic tuning. The transformer feedback of Sharp '161 is not suitable for such an arrangement. In addition, Sharp '594 mentions prior art use of a second coil in the handpiece, adjacent to the excitation coil. The second coil provides the feedback for automatic tuning. Besides the need for an additional coil in the handpiece, Sharp '594 also exhibits some limitations in the automatic tuning of the excitation frequency, and therefore provides manual tuning capabilities to overcome those limitations. It is noted that U.S. Pat. No. 6,190,167, also to Sharp (herein denoted as "Sharp '167"), is a continuation of Sharp '594 and presents no additional material.

U.S. Pat. No. 6,241,520 to Gofman, et al. (herein denoted as "Gofman"), discloses a variation on an oscillator which includes the excitation coil as an integral part of the oscillation circuitry. The inductance of the excitation coil substantially determines the frequency of oscillation of the oscillator. Gofman also features ancillary coils and capacitors ("tank circuits") in the oscillator circuit, so that there are other factors determining the frequency of the oscillation. Thus, as with Sharp '161, as discussed previously, the frequency of oscillation is near, but not exactly at, the resonant frequency of the magnetostrictive insert. Furthermore, Gofman still requires several coils in addition to the excitation coil, thereby incurring additional circuitry complexity and bulk.

U.S. Pat. No. 6,503,081 to Feine (herein denoted as "Feine") discloses the use of a microprocessor to set the frequency of oscillation, such that the power delivered to the excitation coil is maximized. Feine asserts that the microprocessor can be programmed to sense the power input to the excitation coils, perhaps with the use of auxiliary circuitry or components. Feine, however, does not describe how such programming is to be accomplished, nor specifically how to construct such auxiliary circuitry, nor what such auxiliary components might be. But Feine does suggest using voltage-current phase difference measurements or power response slope measurements to determine the maximum power transfer point, in order to set the oscillation frequency to the resonant frequency of the magnetostrictive insert. Although Feine thus suggests a means of reaching the resonant frequency, the requirement for additional power-measurement circuitry imposes further requirements and limitations.

U.S. Pat. No. 6,819,027 to Saraf (herein denoted as "Saraf") discloses a controller for driving current into a piezoelectric transducer through a transformer at a constant frequency and power level. The frequency is found during frequency scans as that which delivers peak load current. Saraf does not discuss how his controller can be used to drive a magnetostrictive device, nor does he consider the complex resonance conditions that characterize such a device, one consequence of which is that peak load current does not necessarily occur at the frequency of peak power transfer; the latter is the more desirable operating point.

Also U.S. Pat. No. 4,525,790 to Nakamura discloses a controller for driving current into an ultrasonic device, wherein the frequency is determined as that which achieves peak load current. This, again, does not ensure peak power transfer.

U.S. Pat. No. 5,431,664 to Ureche et al. (herein denoted as "Ureche") discloses a controller for driving current into an ultrasonic transducer through a transformer while measuring the admittance of the transducer circuit. Ureche advocates operating at a frequency intermediate between series resonance and parallel resonance, attempting to minimize the reactive component of the admittance; he does not, however, teach how to achieve this in a practical and efficient manner, nor does he prove that this would result in maximum power transfer.

U.S. Pat. No. 5,406,503 to Williams, Jr. et al. (herein denoted as "Williams") discloses a controller for driving current into an ultrasonic transducer through a transformer while directly monitoring the power transferred to the transducer. Drive frequency is determined and maintained so as to deliver maximum power. The disadvantage of Williams' controller lies in the elaborate, and thus expensive, arrangement for continuously measuring the power. There is thus a widely recognized need for, and it would be highly advantageous to have, a means of automatically adjusting the oscillation frequency of the excitation current of a magnetostrictive insert to be substantially at the resonant frequency thereof, in a simple and direct manner that does not require feedback coils, tank circuits, or complex circuitry. This goal is achieved by the present invention.

SUMMARY OF THE INVENTION

The present invention is of a method and apparatus for controlling the excitation frequency of current flowing through the excitation coil in which a magnetostrictive insert is placed. In the present application, a dental scaler is used as a non-limiting example of an application for such control method and apparatus. In this non-limiting example, the scaler is used by a dental practitioner in the cleaning of a patient's teeth. The examples and drawings depicting a dental scaler are understood to be for illustrative purposes only, and do not limit the scope of the present invention, which encompasses other dental and comparable medical uses of ultrasonic devices. The terms "magnetostrictive ultrasonic dental device", "ultrasonic device" and "handpiece" are used herein interchangeably, all denoting any ultrasonic apparatus, intended for dental or medical use, which utilizes a magnetostrictive ultrasonic transducer. The control apparatus will also be termed herein as "controller".

It is an objective of the present invention that the frequency be set at an optimal value in a fully automatic manner that does not require any manual adjustment or settings by the practitioner. It is also an objective of the present invention that the frequency be automatically set at an optimal value for a variety of different handpieces and inserts, similarly without requiring any data to be entered by the practitioner.

It is moreover an objective of the present invention that the frequency be continually adjusted for optimal performance, and that the frequency be optimally set each time the practitioner energizes the handpiece, such as by means of a foot-operated switch. In this manner, should the practitioner adjust the power to the handpiece, apply additional pressure to the tip, or change the insert, the control apparatus automatically and continually sets the frequency for optimal performance.

It is furthermore an objective of the present invention that the above operating characteristics be attained through relatively simple and inexpensive circuitry and components, preferably utilizing integrated circuitry to the greatest extent possible, and reducing the need for reactive components, such as coils and capacitors. In keeping with this, it is an objective of the present invention that multiple handpieces, optionally containing inserts of different resonant frequencies, be accommodated without the need for additional complex circuitry.

The primary principle of the control apparatus and the method of operation according to the present invention is to control the frequency of the drive signal to the handpiece so as to maximize the power transferred to the working insert. The frequency corresponding to such maximum power transfer is typically at or near a resonance frequency of the coil-tip assembly and will therefore be referred to herein as resonance frequency, even though resonance (however defined) is not a necessary condition and is not detected as such when controlling the drive frequency. Rather a certain function of the current through the excitation coil is monitored, extracting certain measures therefrom and comparing these measures with corresponding optimal values that correspond to conditions of maximum power transfer. Such optimal values are obtained during infrequent calibration runs, performed on combinations of each type of handpiece and insert to be used—preferably in a laboratory or in the factory, where accurate mechanical- and/or electrical power measuring equipment is available. The advantage of the principle employed in the present invention, as outlined above and as further explained below, is that it obviates the need to include in the controller elaborate circuits and components for directly measuring the power transferred to the magnetostrictive insert—accurately and continuously—replacing them by relatively simple and inexpensive components.

In preferred embodiments of the present invention, the measures that are obtained from the current through the excitation coil are its peak value and the peak value of a high-pass filtered version of the current. In general, however, other measures may be contemplated and similarly compared with optimum values according to the same primary principle of the invention. Such comparisons are carried out during periodic frequency adjustment procedures, each procedure consisting of an iterative process of frequency incrementations or decrementations, alternating with value comparisons and decisions. In preferred embodiments of the present invention there is first a series of coarse frequency increments, then a series of fine frequency decrements until optimum frequency is reached; but, in general, also other schemes of frequency scanning may be used within the concept of the invention.

Therefore, according to the present invention there is provided a controller for driving an excitation current through an excitation coil of a magnetostrictive ultrasonic device, the controller comprising: (a) a source of a periodic signal having a controllable frequency; (b) a driver responsive to said periodic signal and configured to cause an excitation current to flow through the excitation coil commensurate with said periodic signal; (c) a current sensor in series with the excitation coil, operative to output a current-sense signal proportional to the current flowing through the excitation coil; (d) a function block operative to receive said current-sense signal and to output one or more function signals proportional to corresponding predetermined functions thereof; and (e) a digital processor, operative to receive said function signals and to periodically sample them, obtaining corresponding sample function values, and to control the frequency of said periodic signal so that each of said sample function values differs from a corresponding given optimum function value by less than a given threshold value. Preferably each of said optimum function values has been determined so as to correspond to maximum power delivered by the excitation coil.

Preferably the frequency controlling, by said digital processor, is carried out during periodically repetitive frequency adjustment procedures, each of relatively brief duration, and only while the ultrasonic device is active.

In some configurations of the controller, during each of said frequency adjustment procedures the frequency of the periodic signal is swept in steps over a range of frequencies and after each of said steps the latest sample function values are compared with the corresponding optimal function values. Preferably, the steps of frequency sweeping are coarse during a first portion of the procedure and fine during the rest of the procedure.

In some configurations of the controller, the predetermined functions of said current-sense signal are selected from the group consisting of: (a) peak value of said current-sense signal and (b) peak value of a high-pass filtered version of said current-sense signal.

The controller may be configured to drive an excitation current through an excitation coil of any one of a plurality of ultrasonic devices and to further comprise a switch, operative to connect said driver with the excitation coil of any selected one of the ultrasonic devices; wherein said optimum function values are those that correspond to the selected device.

In some configurations of the controller, it further comprises one or more sensors, configured to detect the type of ultrasonic device currently in use and operative to convey its identity to the digital processor.

In some configurations of the controller, it further comprises a transformer, said driver is in series with the primary coil of the transformer and said current sensor and the excitation coil are in series with the secondary coil of the transformer.

In addition, according to the present invention, there is provided a method for controlling the frequency of excitation current flowing in the excitation coil of a magnetostrictive ultrasonic dental device, the method comprising: (i) Applying alternating voltage across the excitation coil, at a controllable frequency; (ii) sensing the excitation current flowing in the excitation coil and generating a current-sense signal proportional to said current; (iii) generating one or more function signals, proportional to corresponding predetermined functions of said current-sense signal; (iv) controlling the frequency of said alternating voltage by running, from time to time, a frequency adjustment procedure, which includes (a) sampling said function signals, to obtain corresponding sample function values; (b) comparing the latest sample function values with corresponding predetermined optimum function values; and (c) if all the differences resulting from said comparisons are less than a given threshold value, leaving the frequency unchanged; otherwise incrementing or decrementing the frequency and repeating steps 'a' to 'c'.

In some configurations of the method according to the present invention, any of said predetermined functions of said current-sense signal is selected from the group consisting of: (a) peak value of said current-sense signal and (b) peak value of a high-pass filtered version of said current-sense signal.

In some configurations of the method according to the present invention, any frequency adjustment procedure includes two consecutive frequency scans; the first frequency scan includes setting the frequency to a given minimum (or maximum) value and then performing steps 'a' to 'c', whereby the frequency is incremented (or decremented) by a coarse step of a given value; the second frequency scan includes performing steps 'a' to 'c', whereby the frequency is decremented (or incremented) by a fine step of a given value, smaller than that of said coarse step.

BRIEF DESCRIPTION OF THE DRAWINGS

The invention is herein described, by way of example only, with reference to the accompanying drawings, wherein.

DESCRIPTION OF THE PREFERRED EMBODIMENTS

The principles and operation of a controller for magnetostrictive ultrasonic dental devices according to the present invention may be understood with reference to the drawings and the accompanying description.

Figure 1:
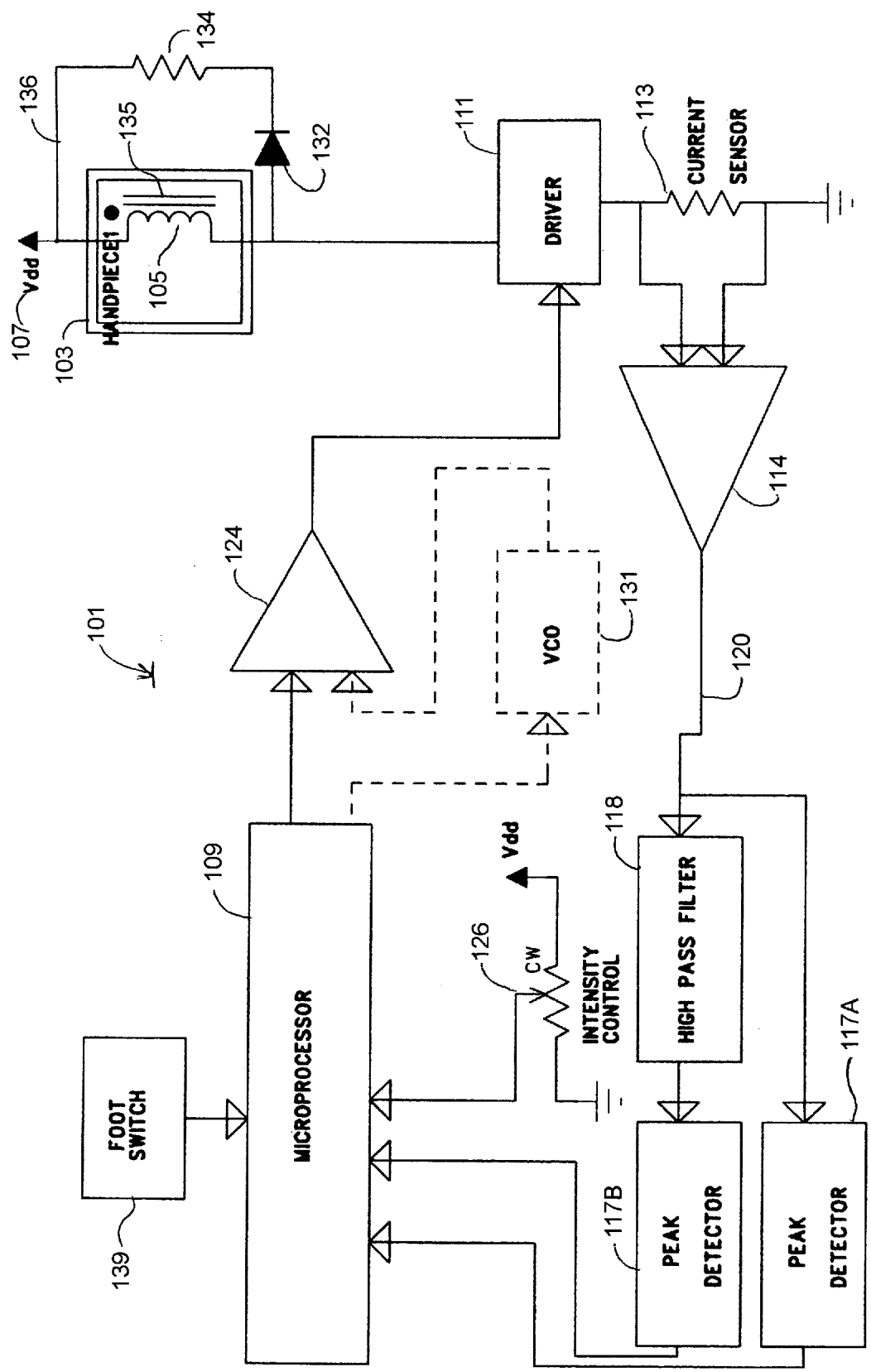
FIG. 1 is a block diagram of a magnetostrictive ultrasonic dental scaler system according to an embodiment of the present invention.

FIG. 1 is a conceptual block diagram of a magnetostrictive dental scaler system according to an embodiment of the present invention. A controller 101 controls the current through an excitation coil 105 in a separate handpiece 103. A magnetostrictive insert 135 is placed within handpiece 103 within excitation coil 105. (Insert 135 is shown schematically in FIG. 1. In practice, insert 135 is placed physically within the confines of excitation coil 105, such that the tip of insert 135 is exposed and available for cleaning the surfaces of the patient's teeth).

Coil 105 is connected, in series with a driver 111 and a current sensor 113, between a voltage source 107, and the other end of coil 105 connects to a return path (e.g. ground)

108. Driver 111 is generally configured to cause an alternating current to flow through this series circuit (including coil 105). It is noted that coil 105 and insert 135 are the only components of the system that are included in any handpiece 103; all other components are referred to collectively as a "controller" and are housed preferably together, their assembly being connected with the handpiece by cable.

In one preferred embodiment, Driver 111 includes an on/off switch, such as a switching transistor, connected in series with the aforementioned circuit, the switch being operative to periodically close and open the circuit—in effect applying a train of voltage pulses across coil 105 (in series with current sensor 113). This train of voltage pulses is illustrated by the waveform 240 in the first row of FIG. 5. They are characterized by a "time on" ($T_{on}$) and a "time off" ($T_{off}$) portion of each cycle. The ratio of $T_{on}$ to the total period of a cycle is termed "duty cycle". Thus the train of voltage pulses may be characterized by its frequency (i.e. pulse rate) and duty cycle (i.e. pulse width). Both of these parameters are variable, as will be explained below. It is noted that in the present exemplary embodiment the amplitude of the pulses is essentially constant; in other embodiments the amplitude may also be made variable.

During $T_{on}$ (i.e. when the switch in Driver 111 is on), the voltage applied across Coil 105 causes an increasing current to flow through it, the rate of the increase at any instant being determined by the reactive characteristics of the coil, as magnetically coupled with the insert 135. During $T_{off}$ (i.e. when the switch in Driver 111 is off), the current continues to flow because of the inductance of the coil and now flows, at a decreasing rate, through a so-called snubber circuit 136, which includes diode 132 and resistor 134. After several pulses from the start of operation, or from a change in any of the parameters, the waveform of the current through the coil (i.e. the current as a function of time) becomes essentially identical from cycle to cycle. A typical current waveform through the coil over three successive pulse periods is shown in the second row of FIG. 5—for two different values of pulse rate, one being at resonance frequency and the other at a frequency off resonance. The significance of the latter is discussed further below. The dashed portions of the wave correspond to current flowing only through snubber circuit 136 (during $T_{off}$), while the solid portions correspond to current flowing through driver 111 and current sensor 113 (during $T_{on}$).

It will be appreciated that also other configurations of the circuit that includes coil 105, driver 111 and current sensor 113 are possible, all coming within the scope of the present invention. For example, driver 111 may be series-connected between Vdd and the parallel combination of coil 105 and snubber circuit 136. As another example, driver 111 may include a power amplifier, whose output is applied in place of Vdd.

The input to driver 111 is generally a periodic signal, whose frequency and duty cycle equal those of the alternating voltage (e.g. pulse train) applied across coil 107. In one preferred embodiment the signal is a binary signal generated in a digital processor, preferably Microprocessor 109, and amplified by buffer amplifier 124; the output of the latter preferably activates the switch in driver 111.

In another embodiment, shown in FIG. 1 by dashed lines (to replace buffer 124, or as an alternative input thereto), the signal input to driver 111 is generated by a voltage-controlled oscillator (VCO) 131, the frequency of this signal is controlled by the analog voltage input to the voltage-controlled oscillator. The latter may be supplied directly from Microprocessor 109 (if thus operative). Alternatively the input voltage to VCO 131 may be obtained as the voltage across a capacitor 129, which is charged through a resistor 127 by a Schmitt trigger 125, whose input is a binary pulse-width modulated signal 123 from microprocessor 109; By varying the duty cycle of this binary signal, microprocessor 109 can alter the voltage across a capacitor 129 and thus—the frequency output from voltage-controlled oscillator 131.

As previously discussed, it is the primary objective of the apparatus and the method of the present invention to control the frequency of the drive signal to the handpiece so as to maximize the power delivered by the excitation coil (i.e. the power transferred from it to the working insert). In embodiments of the controller according to the present invention, the frequency is adjusted so as to bring a certain function of the current through the excitation coil close to optimum values, determined for each type of handpiece and/insert during a calibration procedure, preferably in a laboratory.

Current sensor 113 generally serves to sense the current flowing through coil 105, at least during $T_{on}$ periods, producing a signal analogous to it, to be termed "current-sense signal". In a preferred embodiment of the present invention, current sensor 113 includes a resistor with a relatively low resistance value, so that the voltage drop across it is proportional to the current flowing through coil 105 during $T_{on}$ periods. This voltage drop is then amplified by buffer amplifier 114 and thus becomes the current-sense signal 120.

Figure 1A:
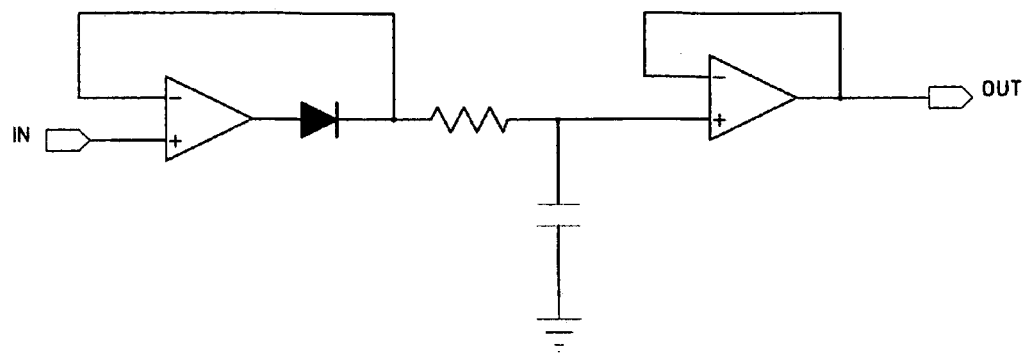
FIG. 1A and FIG. 1B are schematic circuit diagrams of certain components in the system of FIG. 1.
Figure 5:
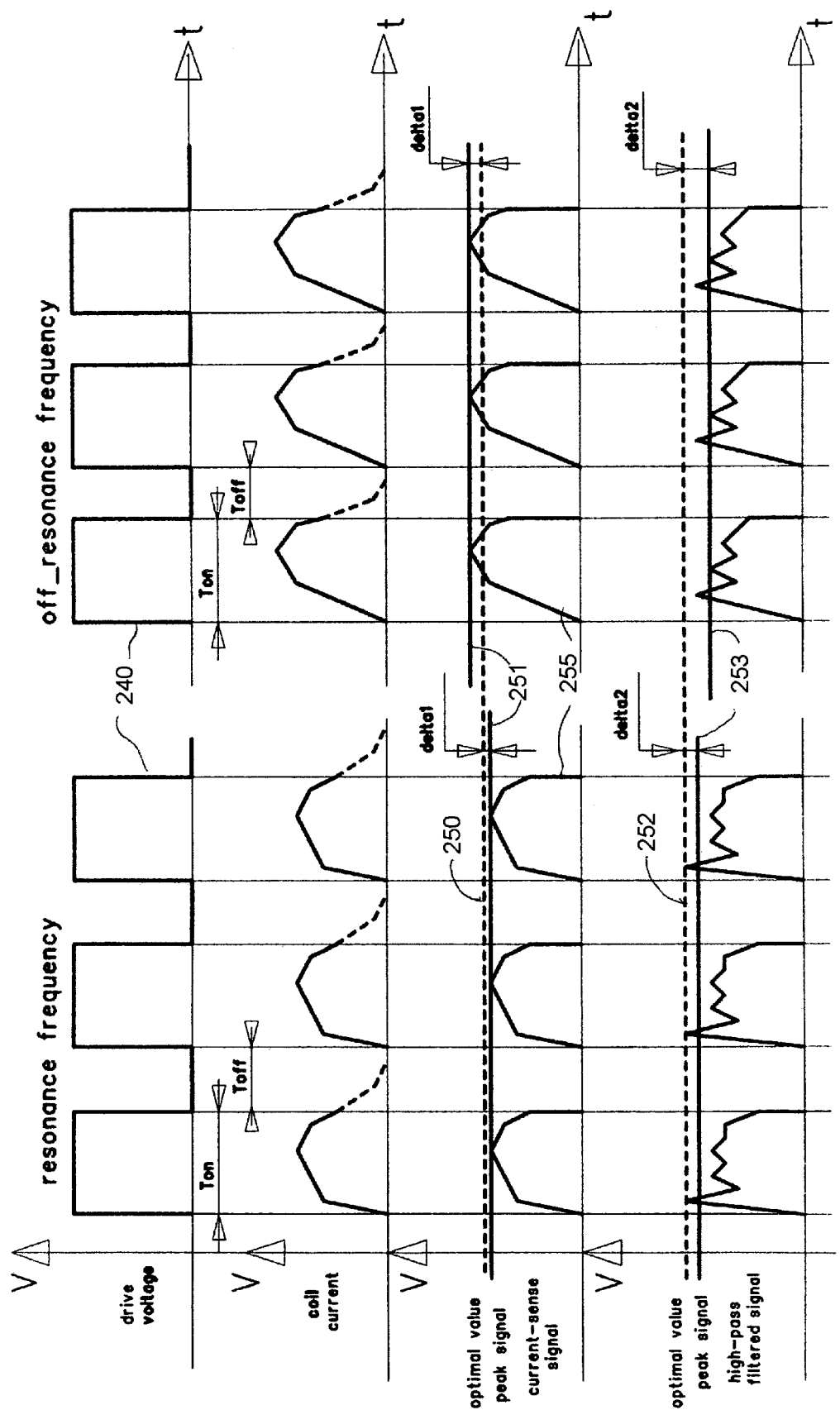
FIG. 5 is a schematic waveform diagram, depicting typical signals in an embodiment of the present invention.

Signal 120 is preferably applied along two paths. In the first path it is applied to peak detector 117A, which is operative to continuously detect the periodic peak values (i.e. the peak of each period, or cycle) of the current-sense signal 120 (which correspond to the periodic peak values of the alternating current through coil 105) and to output a corresponding periodic peak signal. The third row of FIG. 5 shows schematically a typical waveform of the current-sense signal 255, as well as the corresponding currently detected peak signal 251; this is shown for two different pulse frequencies—one close to resonance and one off resonance. The peak detector may include, for example, an operational amplifier with a diode in its output circuit, as shown in FIG. 1A; however many other devices known in the art may be used for the purpose.

Figure 1B:
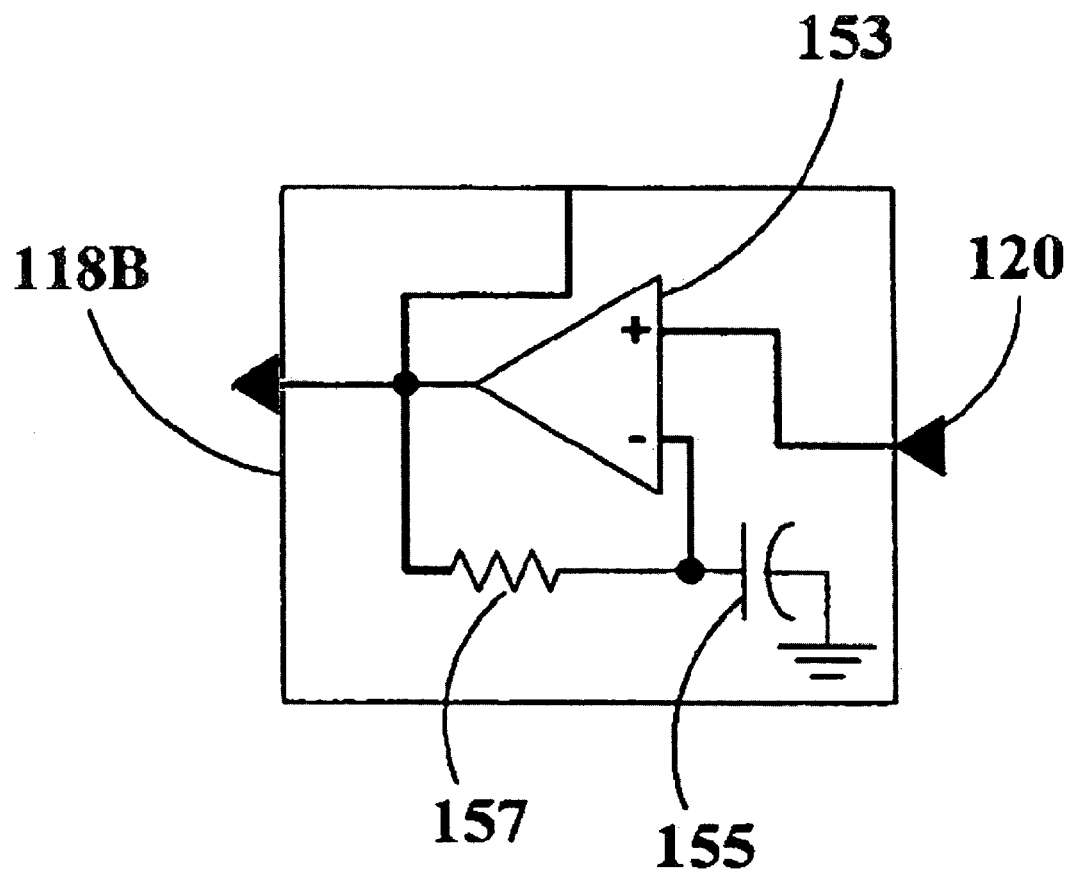

In the second path, current-sense signal 120 is applied to a high-pass filter 118. The latter may, for example, be a circuit 118B, as schematically shown in FIG. 1B, which includes an operational amplifier 153, whose non-inverting input receives the signal 120, and whose inverting input receives feedback through a resistor 157 and is returned to ground through a capacitor 155; however many other devices known in the art may be used as the high-pass filter. The fourth row of FIG. 5 shows schematically a typical waveform of the output signal from high-pass filter 118. It is noted that this waveform typically has more pronounced high-frequency components, which are largely harmonics of the fundamental pulse frequency. It is also noted that high-pass filtering, as is the function of filter 118, approximates the function of combining the current-sense signal 120 with a time-derivative of itself. The output of high-pass filter 118 is applied to a second peak detector 117B, which is similar in structure and operation to the first peak detector 117A and whose typical detected periodic peak signal is shown in FIG. 5 as line 253.

High-pass filter 118 and peak detectors 117A and 117B are herein collectively referred to as a "function block" and represent a preferred embodiment thereof. There are, however, many other embodiments and configurations of a function block possible within the context of the present invention. All are characterized by having a current-sense signal as input and one or more function signals derived therefrom according to some functions—as output. They are further characterized by the ability to establish values for the output signals that are uniquely indicative of a state of resonance at the current rate (or frequency) of pulses applied to the coil 105; typically such values would be established empirically, e.g. in a calibration procedure, but analytic methods to establish the values are not excluded. The function signal output from each of the two aforementioned paths, is proportional to a corresponding specific function of the current-sense signal. There are, however, in general, many functions, other than that those performed by the function block in the present embodiment, described above, that could thus be embodied in the context of the present invention, which would lead to function signals other than the periodic peak signals. Also, the number of various functions embodied in any one controller may be different than two, as it is in the present embodiment—for example one or three or more.

The periodic peak signals from peak detectors 117A and/or 117B are fed to microprocessor 109—preferably applied to one or two corresponding analog inputs thereof; alternatively they may be applied to microprocessor 109 through one or two corresponding A/D converters (not shown). The resultant digital sample values of the two periodic peak signals (or of the function signals in general), referred to as "sample function values", are continuously stored in respective registers (or memory cells), which thus hold, at any instant, the latest pair of values. Microprocessor 109 is operative to digitally process the peak signals in a series of steps during a "frequency adjustment procedure", to be further explained below, as follows: There are stored preferably two "optimal peak values"—one for the peak value of the current-sense signal (as output, for example, by peak detector 117A) and one for the peak value of the signal's high-pass filtered version (as output, for example, by peak detector 117B). The optimal peak values are determined off-line, preferably during a factory- or laboratory calibration process, as those corresponding to a pulse frequency at which maximum power is delivered by the excitation coil of the handpiece to the insert (which, as noted before, is referred to as the resonance frequency). There is stored a pair of such optimal peak values preferably for each type of handpiece and insert combination, each being associated with a nominal resonance frequency (typically 25 or 30 KHz). Also stored for each such resonance frequency is the minimum and maximum values of the range of frequencies that straddles it.

At each step and for each of the two periodic peak signals a sample value is extracted, at the end of a given brief time period (e.g. 7 milliseconds), and compared with its respective optimal value; the difference is noted as a respective delta value. The third and fourth waveform rows in FIG. 5 illustrate these comparisons for the two exemplary pulse frequencies (showing, for conciseness, only a three pulse periods); the third row relates to the current-sense signal and the fourth row—to its high-pass filtered version. In each row there is shown the corresponding optimal peak value, as line 250 or 252, respectively, as well as the corresponding peak signal, as line 251 or 253, respectively. In each case the gap between the optimal peak value and the peak signal is marked as delta1 in the third row) or delta2 (in the fourth row). In continuing the step, each delta value is compared with a given fixed threshold value; if both delta values are less than the threshold, a state of resonance is indicated; if any of the delta values exceeds the threshold, the processor proceeds to the next step, as explained below, wherein the pulse frequency is changed and the peak values extraction and comparison operation is repeated, as described hereabove. When a state of resonance is indicated, the current pulse frequency is registered and microprocessor 109 continues to output to buffer 124 a train of pulses at that frequency.

Preferably there is provided means for automatically identifying the type of handpiece or insert being currently used; alternatively, the identity of the type can be entered in a keyboard by the operator. In any case, the identity is communicated to microprocessor 109 and the optimal peak values (to be applied as explained hereabove) are selected from storage accordingly. Also selected accordingly from storage are the aforementioned minimum and maximum values of the range of frequencies that are applicable to the type (which range is typically centered on the resonance frequency).

Intensity control 126, connected to microprocessor 109, is operative to enable the operator to set the intensity, or level, of the power delivered to the handpiece (and thus—the intensity of the vibrations in insert 125). In the preferred embodiment, shown in FIG. 1, it includes a potentiometer, whose output value is fed to an analog input of the microprocessor; any other means known in the art may be used instead, including, for example, a digital register with input buttons or entry via a keyboard. According to the value input from intensity control 126, microprocessor 109 sets a corresponding duty cycle in its output signal. When the duty cycle is near 50%, the amplitude of the fundamental frequency component (whose frequency is equal to the pulse rate) of the current flowing through coil 105 is near its maximum and so is the power level delivered by it to the insert. During the frequency adjustment procedure (see above), the duty cycle is preferably set to a predetermined value and at the end of that procedure it reverts to the value that corresponds to the current intensity control setting. It is noted that also during the above-mentioned factory calibration process the duty cycle is set to that same predetermined value.

Operation of the system generally proceeds as follows: The ultrasonic device is turned active, i.e. ultrasonic vibration is initiated, by the action of the practitioner, typically by pressing on a foot-operated switch 139. Foot switch 139 is considered to be either in an "on" state or in an "off" state. In an embodiment of the present invention, the "on" state occurs when foot switch 139 is depressed, and the "off" state occurs when foot switch 139 is not depressed. When the practitioner depresses switch 139, it signals microprocessor 109 to output a train of pulses, thus enabling driver 111 to allow time-varying current to flow through coil 105—all as explained, for example, hereabove. When switch 139 is not depressed, however, no pulses are output by the microprocessor and thus no current is driven by driver 111 or flows through coil 105. All along, the current through driver 111 flows also through current sensor 113. Immediately after the foot switch is placed in the "on" state, a frequency adjustment procedure is initiated in microprocessor 109 in order to set the frequency of the output pulse train to the resonance frequency of the currently used handpiece-insert combination. The procedure during the frequency adjustment procedure is explained below, as part of the overall operation, with reference to FIG. 2.

Figure 2:
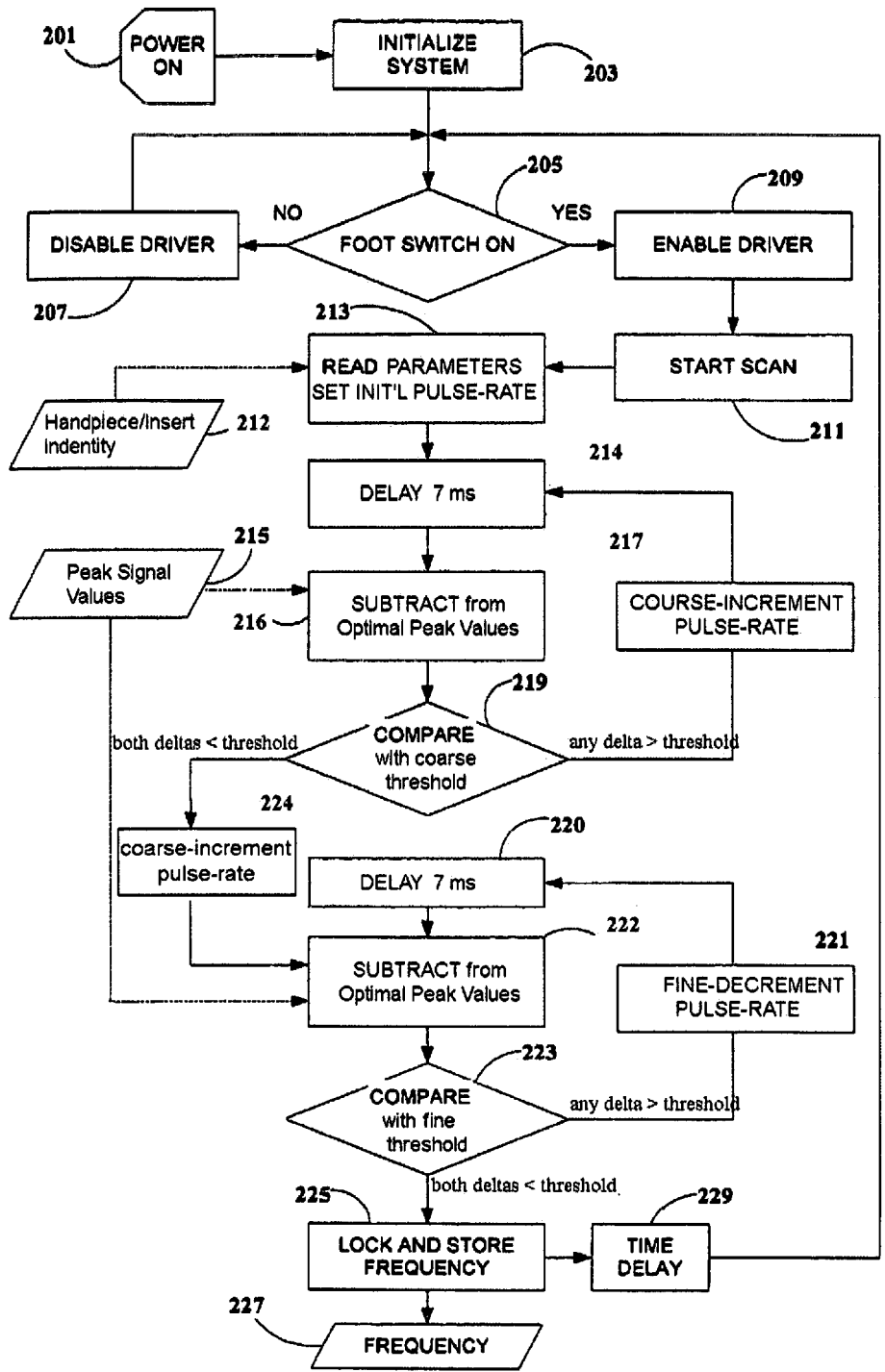
FIG. 2 is a flowchart of a method for controlling a magnetostrictive ultrasonic dental scaler device according to an embodiment of the present invention.

FIG. 2 is a flowchart of a method according to the present invention for setting the frequency of the current flowing through the excitation coil. This method requires having a means of generating a controllable frequency for the excitation current and a means of sensing the excitation current. These and other required components are, for example, those referenced to in FIG. 1 and explained in the previous discussion. After a power-on operation 201, the controller is initialized in a step 203. Then, at a decision point 205, the foot switch (switch 139 in FIG. 1) is checked. If the foot switch is not depressed, then the excitation coil driver (driver 111 in FIG. 1) is disabled and decision point 205 is repeatedly checked, as shown. If the foot switch is depressed, then the excitation coil driver is enabled, and the frequency adjustment procedure is initiated in a step 211.

The frequency adjustment procedure consists of an initiation and two consecutive frequency scans, the first being a coarse scan and the second—a fine scan. It starts, in a step 213, with reading from storage the minimum frequency and the two optimal peak values that correspond to the currently used type handpiece and insert, as automatically detected or manually entered (data element 212), and then setting the initial pulse rate to the minimum frequency. After a brief time delay (step 214)—typically 7 milliseconds—the current values of the two peak signals (output by peak detectors 117A and 117B of FIG. 1 and digitized) are read from their respective registers, or memory cells (data element 215). These are subtracted (step 216) from the respective optimal peak values and the differences—delta1 and delta2, respectively—noted; these terms are explained above, with reference to FIG. 5.

At a decision point 219, delta1 and delta2 are compared with their respective coarse threshold values: If both delta values are below their thresholds, the pulse rate is incremented one coarse step (step 224) and the fine scan is initiated at step 222 (see below); if, however, any of the delta values exceeds its threshold, then the pulse rate is incremented one coarse step (step 217) and after another brief delay (step 214), steps 216 and 219 are repeated in the same manner until the fine frequency scan is initiated at step 222.

At step 222 the current peak signal values (data element 215) are, again, subtracted from the respective optimal peak values (as read in step 213) and the resultant differences—delta1 and delta2, respectively—are noted. At a decision point 223, delta1 and delta2 are compared with their respective fine threshold values: If any of the delta values exceeds its threshold, then the pulse rate is decremented one fine step (step 221) and after a brief delay (step 220), steps 216 and 219 are the function f of the current is higher, then steps 222 and 223 are repeated. If, however, both delta values are below their thresholds, then in a step 225 the frequency (i.e. the latest pulse rate) is locked and stored in a data element 227. This ends the frequency adjustment procedure. It is noted that, since the frequency adjustment procedure ends as soon as the correct frequency has been reached, its duration is generally variable and is, on the average, shorter than fixed protocol procedures in some prior art, in which the whole frequency range is scanned every time.

At step 229, a predetermined time delay is imposed, after which the foot switch state is checked again in step 205. In this manner, the frequency is repeatedly adjusted to achieve optimum power transfer to the excitation coil. According to an embodiment of the present invention, the frequency adjustment procedure can be performed at regular time intervals, thus continually updating the frequency to take into account changing conditions. Moreover, if the practitioner interchanges inserts during a procedure, a controller according to the present invention will automatically find the optimum frequency regardless of the operating characteristics of the new insert. In an embodiment of the present invention, the frequency adjustment procedure is held in abeyance when the foot switch is released.

It is noted that in some prior art, such as that of Feine, the frequency is scanned and adjusted before the foot switch is depressed, thus setting the frequency under a no-load condition, rather than during actual operating conditions as performed according to the present invention.

In an embodiment of the present invention, the frequency increase in step 217 is a "coarse" (or relatively large) frequency increase, whereas the frequency decrease in step 221 is a "fine" (or relatively small) frequency decrease. In this embodiment, the frequency is first scanned coarsely with increasing frequency, and then when the optimum operating point has been passed, the frequency is scanned finely with decreasing frequency until the optimum operating point is reached. In another embodiment, the frequency is first scanned coarsely with decreasing frequency, and then when the optimum operating point has been passed, the frequency is scanned finely with increasing frequency until the optimum operating point is reached.

In other embodiments of the present invention, the frequency adjustment procedure as described above may be replaced, at least some of the times, by a "frequency check-and-correct procedure"; according to the latter, the sample function values are compared, from time to time, with their corresponding optimum function values and only when any difference exceeds its threshold value, is a full frequency adjustment procedure conducted. In a variation of this procedure, the frequency is incremented or decremented from its last checked value (instead of first setting it at the maximum or minimum of the range, as described above). One possibility is to run the coarse frequency scan from the last checked value by alternately incrementing and decrementing the frequency by ever increasing steps; the fine scan would then follow as before. Another possibility is to immediately run the fine frequency scan from the last checked value—again by alternately incrementing and decrementing the frequency by ever increasing steps.

Figure 3:
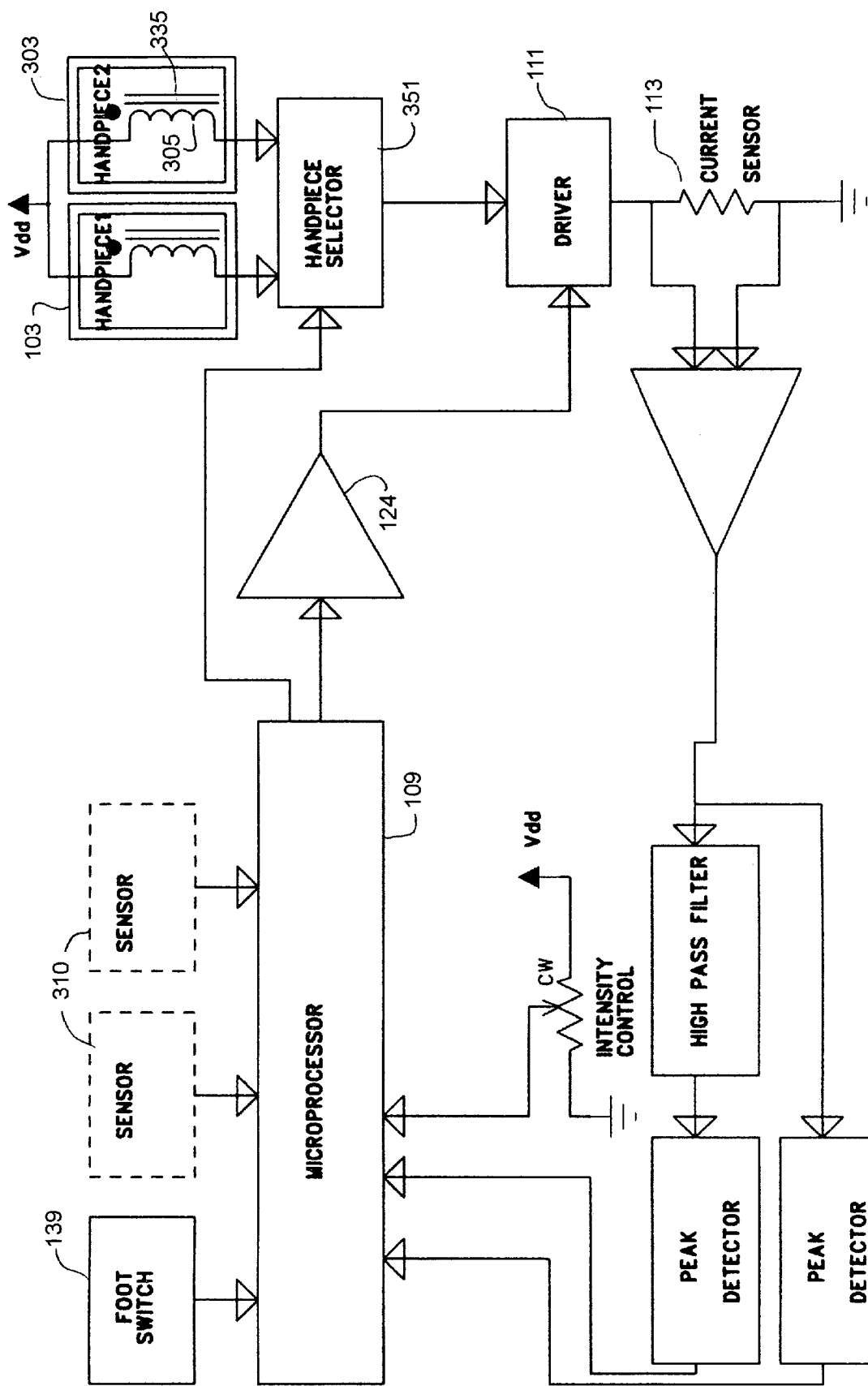
FIG. 3 is a block diagram of a magnetostrictive ultrasonic dental scaler system, having multiple handpieces, according to another embodiment of the present invention.

FIG. 3 illustrates a configuration, according to the invention, that has a plurality of ultrasonic devices—e.g. an additional handpiece 303, containing an excitation coil 305 and an insert 335. It is similar, in structure and function, to the configuration of FIG. 1 except that, instead of driver 111 being connected directly to excitation coil 105, the output of driver 111 goes to a handpiece selector 351, which connects driver 111 either to coil 105 or to coil 305. Microprocessor 109 controls handpiece selector 351 to make the appropriate selection. The selection may be entered into the microprocessor manually, but preferably it is entered by having a sensor 310 at the holder of each handpiece; when the practitioner pulls a handpiece for operation, the respective sensor signals microprocessor 109 to effect the corresponding selection in selector 305. At the same time the identity of the selected handpiece is noted, to be used in setting the pulse rate—e.g. during frequency adjustment procedures (data point 212 in FIG. 2). More than two handpieces are also possible in a similar way. In this manner, a practitioner can have multiple handpieces with different inserts installed for rapid deployment during a procedure.

Figure 4:
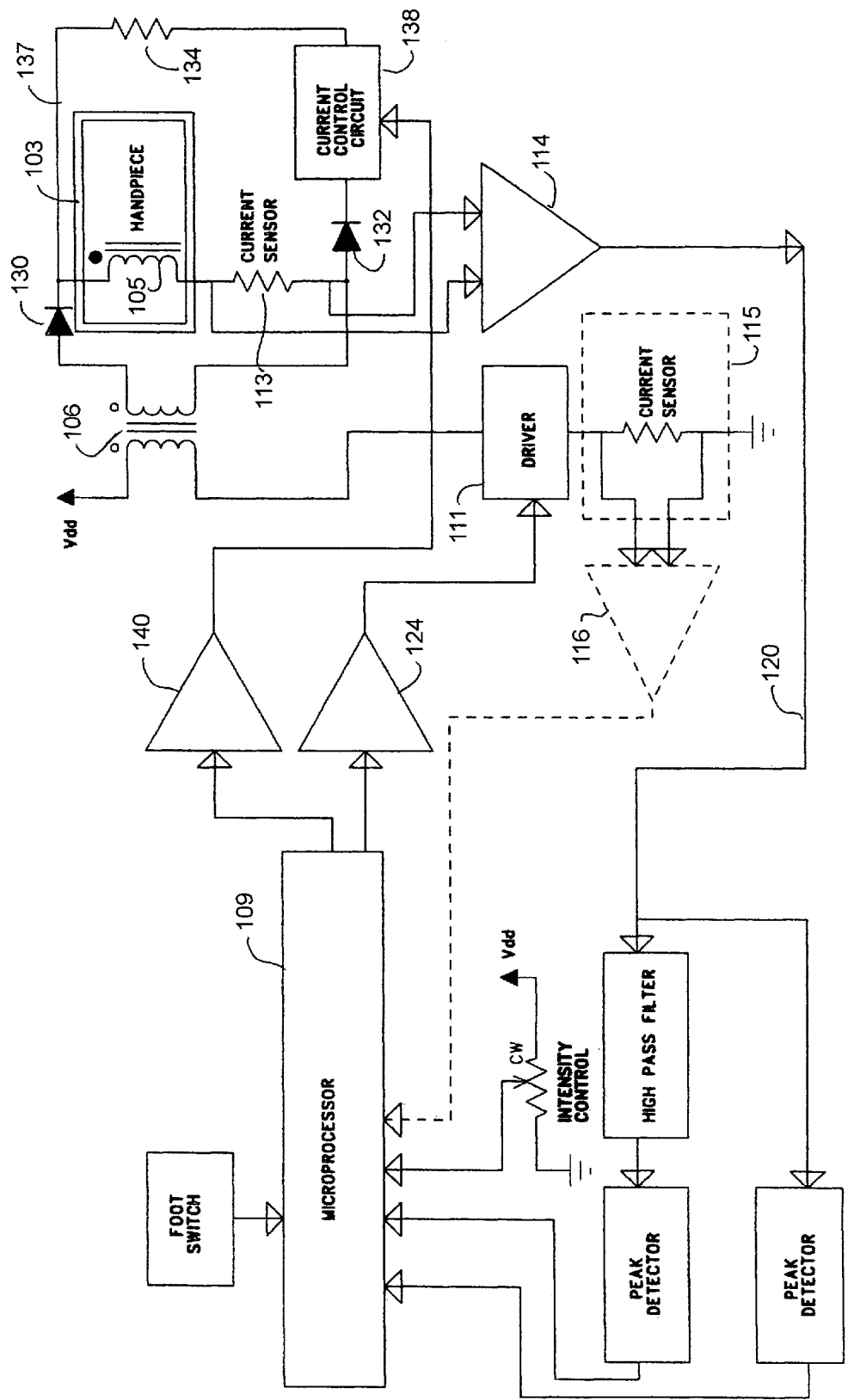
FIG. 4 is a block diagram of a magnetostrictive ultrasonic dental scaler system according to yet another embodiment of the present invention.

FIG. 4 illustrates another configuration, according to the invention, which is similar, in structure and function, to the configuration of FIG. 1 except that the excitation coil (in handpiece 103) is not connected directly in series with driver 111, as is the case in the configuration of FIG. 1; rather, excitation coil 105 is coupled to the driver circuit through a transformer 106. Moreover, in this configuration current sensor 113 is connected, again, in series with coil 105 but not anymore in series with driver 111. An advantage of this configuration is that it eliminates the flow of direct current through the excitation coil, which does not contribute to the ultrasonic energy but causes annoying heating of the handpiece.

More particularly, in a preferred embodiment of the configuration of FIG. 4, the primary coil of transformer 106 is connected in series between driver 111 and the voltage source Vdd. The secondary coil of transformer 106 is connected across the series combination of diode 130 coil 105 and current sensor 113. In addition there is connected, across the series combination of coil 105 and current sensor 113, a snubber circuit 137, which includes, in series, a resistor 134, a diode 132 and a Current Controller 138. Current Controller 138 is preferably an on/off switch, which is activated by signal from Microprocessor 109, through buffer amplifier 140; its purpose is to control the total current flowing through coil 105 during $T_{off}$ and thus, in effect—the average power delivered to the coil and the insert.

With additional reference to FIG. 5, operation of the current driving circuits of the configuration of FIG. 4 is preferably as follows: According to the pulsed signal from Microprocessor 109 (through buffer 124), Driver 111 switches between on- and off states—$T_{on}$ and $T_{off}$. During $T_{on}$, voltage is applied across the primary coil of transformer 106, which causes a similar voltage across the secondary coil—again as shown in the first row of FIG. 5. This, in turn, causes a current to flow, in a generally increasing manner, through diode 130, coil 105 and current sensor 113. During $T_{off}$, essentially no voltage is applied across the transformer's coils, but Current Controller 138 (which is otherwise in an open-switch state) is made to be in a closed-switch state during all, or some portion, of $T_{off}$; owing to the inductance of excitation coil 105, current continues to flow, in a generally decreasing manner, through it and through snubber circuit 137 (i.e. through diode 132, Current Controller 138 and resistor 134). The resultant waveform of the current through the excitation coil is again typically as shown schematically in the second row of FIG. 5. Operation of the rest of the system, notably the function block (e.g. the high-pass filter and the peak detectors), is essentially as described above for the configuration of FIG. 1, even though the waveform of the current sense signal (third row of FIG. 5) is now different and resembles that of the current through coil 105 (second row).

Optionally the configuration of FIG. 4 also includes a current sensor 115 (preferably a low-value resistor) in series with driver 111 and the primary coil of transformer 106. The signal voltage across current sensor 115 is amplified by buffer 116 and applied to microprocessor 109. The purpose of this addition is to enable measuring and controlling the current through the primary coil, as may be required, for example, when varying the duty cycle or amplitude of the applied voltage for controlling the power into the excitation coil.

Clearly there are also other configurations possible, such as, for example, those that combine the additional features of FIG. 3 and FIG. 4—all coming within the scope of the present invention. While the invention has been described with respect to a limited number of embodiments, it will be appreciated that many variations, modifications and other applications of the invention may be made.

We claim:

1. A controller for driving an excitation current through an excitation coil of a magnetostrictive ultrasonic device, the controller comprising:
   A source of a periodic signal having a controllable frequency;
   a driver responsive to said periodic signal and configured to cause an excitation current to flow through the excitation coil commensurate with said periodic signal;
   a current sensor in series with the excitation coil, operative to output a current-sense signal proportional to the current flowing through the excitation coil;
   A high pass filter, receptive to said current sense signal and operative to output a high-pass filtered version thereof;
   a first peak detector, receptive to said current sense signal and operative to output a first peak signal, proportional to the periodic peak value thereof;
   a second peak detector, receptive to said high-pass filtered version and operative to output a second peak signal, proportional to the periodic peak value thereof; and
   a digital processor, operative—
      to receive said first and second peak signals and to periodically sample them, obtaining corresponding sample function values, and—
      to control the frequency of said periodic signal so that each of said sample function values differs from a corresponding given optimum function value by less than a given threshold value.

2. A controller for driving an excitation current through an excitation coil of any one of a plurality of magnetostrictive ultrasonic devices, the controller comprising—
   a plurality of sensors, each configured to sense the presence of a corresponding one of the ultrasonic devices at its respective holder and operative, upon removal of any one of said devices, to issue a corresponding selection signal;
   a source of a periodic signal having a controllable frequency;
   a driver responsive to said periodic signal and configured to cause an excitation current to flow through the excitation coil commensurate with said periodic signal;
   a selector, operative to connect said driver with the excitation coil of any one of the ultrasonic devices according to said selection signal;
   a current sensor in series with said driver, operative to output a current-sense signal proportional to the current flowing through the excitation coil;
   a function block operative to receive said current-sense signal and to output one or more function signals proportional to corresponding predetermined functions thereof; and
   a digital processor, operative—
      to receive said selection signals;
      to receive said function signals and to periodically sample them, obtaining corresponding sample function values, and—
      to control the frequency of said periodic signal so that each of said sample function values differs from a corresponding given optimum function value, selected according to the received selection signal, by less than a given threshold value.

3. A method for controlling the frequency of excitation current flowing in the excitation coil of a magnetostrictive ultrasonic device, the method comprising:
   (i) Applying alternating voltage across the excitation coil, at a controllable frequency;
   (ii) sensing the excitation current flowing in the excitation coil and generating a current-sense signal proportional to said current;
   (iii) generating two or more function signals, proportional to corresponding predetermined functions of said current-sense signal;
   (iv) controlling the frequency of said alternating voltage by running, from time to time, a frequency adjustment procedure, which includes—
      (a) sampling said function signals, to obtain corresponding sample function values;
      (b) comparing the latest sample function values with corresponding predetermined optimum function values; and (c) if all the differences resulting from said comparisons are less than a given threshold value, leaving the frequency unchanged; otherwise incrementing or decrementing the frequency and repeating steps 'a' to 'c';

wherein any of said predetermined functions of said current-sense signal is selected from the group consisting of: (a) peak value of said current-sense signal, (b) peak value of a high-pass filtered version of said current-sense signal and (c) peak value of the time-derivative of said current-sense signal.

* * * * *